United States Patent
Contiliano et al.

(10) Patent No.: US 7,972,373 B2
(45) Date of Patent: Jul. 5, 2011

(54) BALLOON EXPANDABLE BIOABSORBABLE STENT WITH A SINGLE STRESS CONCENTRATION REGION INTERCONNECTING ADJACENT STRUTS

(75) Inventors: Joseph H. Contiliano, Stewartsville, NJ (US); Qiang Zhang, Annandale, NJ (US)

(73) Assignee: Advanced Technologies and Regenerative Medicine, LLC, Raynham, MA (US)

( * ) Notice: Subject to any disclaimer, the term of this patent is extended or adjusted under 35 U.S.C. 154(b) by 0 days.

(21) Appl. No.: 11/959,634

(22) Filed: Dec. 19, 2007

(65) Prior Publication Data
US 2009/0163989 A1 Jun. 25, 2009

(51) Int. Cl.
*A61F 2/06* (2006.01)

(52) U.S. Cl. ....... 623/1.15; 623/1.16; 623/1.2; 623/1.34

(58) Field of Classification Search ........ 623/1.15–1.17, 623/1.2, 1.34
See application file for complete search history.

(56) References Cited

U.S. PATENT DOCUMENTS

| | | |
|---|---|---|
| 4,830,003 A | 5/1989 | Wolff et al. |
| 5,085,629 A | 2/1992 | Goldberg et al. |
| 5,102,417 A | 4/1992 | Palmaz |
| 5,104,404 A | 4/1992 | Wolff |
| 5,670,161 A | 9/1997 | Healy et al. |
| 5,709,713 A | 1/1998 | Evans et al. |
| 5,911,754 A * | 6/1999 | Kanesaka et al. ........ 623/1.15 |
| 5,922,020 A | 7/1999 | Klein et al. |
| 5,922,021 A | 7/1999 | Jang |
| 5,954,743 A | 9/1999 | Jang |
| 6,022,371 A | 2/2000 | Killion |
| 6,039,755 A | 3/2000 | Edwin et al. |
| 6,053,943 A | 4/2000 | Edwin et al. |
| 6,080,177 A | 6/2000 | Igaki et al. |
| 6,174,330 B1 | 1/2001 | Stinson |
| 6,203,569 B1 | 3/2001 | Wijay |
| 6,241,760 B1 | 6/2001 | Jang |
| 6,241,762 B1 | 6/2001 | Shanley |
| 6,325,821 B1 | 12/2001 | Gaschino et al. |
| 6,348,065 B1 | 2/2002 | Brown et al. |
| 6,409,761 B1 | 6/2002 | Jang |
| 6,428,570 B1 | 8/2002 | Globerman |
| 6,475,237 B2 | 11/2002 | Drasler et al. |
| 6,488,702 B1 | 12/2002 | Besselink |

(Continued)

FOREIGN PATENT DOCUMENTS

WO WO 2007/021706 A1 2/2007

(Continued)

OTHER PUBLICATIONS

International Search Report and Written Opinion for International Patent Application No. PCT/US2008/087156, mailed Feb. 17, 2009.

(Continued)

*Primary Examiner* — David Isabella
*Assistant Examiner* — Yashita Sharma

(57) ABSTRACT

An expandable, implantable medical device, such as an intraluminal stent fabricated from polymeric materials, includes a plurality of elongated struts in consecutive series and alternating stress concentration junctions interconnecting ends of adjacent struts. When the stent is in an expanded condition, the adjacent struts form expanded substantial V-shapes and stresses are concentrated within the junctions. The junctions define pivot points for the respective attached, adjacent struts. Each of the pivot points is located substantially on a line bisecting the V-shapes formed by the struts, when the stent is expanded.

12 Claims, 3 Drawing Sheets

U.S. PATENT DOCUMENTS

| | | |
|---|---|---|
| 6,524,334 B1 | 2/2003 | Thompson |
| 6,533,809 B2 | 3/2003 | Von Oepen |
| 6,540,774 B1 | 4/2003 | Cox |
| 6,540,775 B1 | 4/2003 | Fischell et al. |
| 6,562,065 B1 | 5/2003 | Shanley |
| 6,602,281 B1 | 8/2003 | Klein |
| 6,602,282 B1 | 8/2003 | Yan |
| 6,626,939 B1 | 9/2003 | Burnside et al. |
| 6,699,278 B2 | 3/2004 | Fischell et al. |
| 6,706,061 B1 | 3/2004 | Fischell et al. |
| 6,730,116 B1 | 5/2004 | Wolinsky et al. |
| 6,736,842 B2 | 5/2004 | Healy et al. |
| 6,743,388 B2 | 6/2004 | Sridharan et al. |
| 6,749,629 B1 | 6/2004 | Hong et al. |
| 6,764,507 B2 | 7/2004 | Shanley et al. |
| 6,770,088 B1 | 8/2004 | Jang |
| RE38,711 E | 3/2005 | Igaki et al. |
| 6,929,657 B2 | 8/2005 | Gomez et al. |
| 6,932,930 B2 | 8/2005 | DeSimone et al. |
| 6,942,689 B2 | 9/2005 | Majercak |
| 6,964,680 B2 | 11/2005 | Shanley |
| 6,991,647 B2 | 1/2006 | Jadhav |
| 6,997,948 B2 | 2/2006 | Stinson |
| 6,998,060 B2 | 2/2006 | Tomonto |
| 7,014,654 B2 | 3/2006 | Welsh et al. |
| 7,060,088 B1 | 6/2006 | Fischell et al. |
| 7,083,642 B2 | 8/2006 | Sirhan et al. |
| 7,128,862 B2 | 10/2006 | Wang |
| 7,135,038 B1 | 11/2006 | Limon |
| 7,169,174 B2 | 1/2007 | Fischell et al. |
| 7,179,288 B2 | 2/2007 | Shanley |
| 7,208,010 B2 | 4/2007 | Shanley et al. |
| 7,208,011 B2 | 4/2007 | Shanley et al. |
| 7,279,004 B2 * | 10/2007 | Shanley ............ 623/1.15 |
| 2001/0044651 A1 | 11/2001 | Steinke et al. |
| 2002/0045668 A1 | 4/2002 | Dang et al. |
| 2002/0055721 A1 | 5/2002 | Palasis et al. |
| 2002/0188346 A1 | 12/2002 | Healy et al. |
| 2003/0004567 A1 | 1/2003 | Boyle et al. |
| 2003/0039696 A1 | 2/2003 | Porter |
| 2003/0060874 A1 | 3/2003 | Igaki |
| 2003/0069630 A1 * | 4/2003 | Burgermeister et al. .... 623/1.15 |
| 2003/0074051 A1 | 4/2003 | Luehrs |
| 2003/0083732 A1 | 5/2003 | Stinson |
| 2003/0105511 A1 | 6/2003 | Welsh et al. |
| 2003/0120280 A1 | 6/2003 | Roller et al. |
| 2003/0125802 A1 | 7/2003 | Callol et al. |
| 2003/0149469 A1 | 8/2003 | Wolinsky et al. |
| 2003/0216806 A1 | 11/2003 | Togawa et al. |
| 2003/0224033 A1 | 12/2003 | Li et al. |
| 2004/0006382 A1 | 1/2004 | Sohier |
| 2004/0054400 A1 | 3/2004 | Granada |
| 2004/0056384 A1 | 3/2004 | Hill et al. |
| 2004/0088044 A1 | 5/2004 | Brown et al. |
| 2004/0131808 A1 | 7/2004 | Schoenie et al. |
| 2004/0148014 A1 | 7/2004 | Nuutinen et al. |
| 2004/0167615 A1 | 8/2004 | Lenz |
| 2004/0172125 A1 | 9/2004 | Burgermeister |
| 2004/0176834 A1 | 9/2004 | Brown et al. |
| 2004/0193241 A1 | 9/2004 | Stinson |
| 2004/0215330 A1 | 10/2004 | Igaki |
| 2004/0220661 A1 | 11/2004 | Shanley et al. |
| 2004/0249442 A1 | 12/2004 | Fleming et al. |
| 2004/0249450 A1 | 12/2004 | Ishii |
| 2004/0253203 A1 | 12/2004 | Hossainy et al. |
| 2004/0260386 A1 | 12/2004 | Shalaby |
| 2005/0021131 A1 | 1/2005 | Venkatraman et al. |
| 2005/0036945 A1 | 2/2005 | Thomas et al. |
| 2005/0059991 A1 | 3/2005 | Shanley |
| 2005/0075716 A1 | 4/2005 | Yan |
| 2005/0098914 A1 | 5/2005 | Varma et al. |
| 2005/0107865 A1 | 5/2005 | Clifford et al. |
| 2005/0123582 A1 | 6/2005 | Sung et al. |
| 2005/0137678 A1 | 6/2005 | Varma |
| 2005/0149162 A1 | 7/2005 | Tenhuisen et al. |
| 2005/0149172 A1 | 7/2005 | Varma |
| 2005/0163821 A1 | 7/2005 | Sung et al. |
| 2005/0187615 A1 | 8/2005 | Williams et al. |
| 2005/0216074 A1 | 9/2005 | Sahatjian et al. |
| 2005/0228492 A1 | 10/2005 | DeSimone et al. |
| 2005/0261760 A1 | 11/2005 | Weber |
| 2005/0283228 A1 | 12/2005 | Stanford |
| 2006/0020330 A1 | 1/2006 | Huang et al. |
| 2006/0030931 A1 | 2/2006 | Shanley |
| 2006/0034769 A1 | 2/2006 | Kohn et al. |
| 2006/0036312 A1 | 2/2006 | Tomonto |
| 2006/0036316 A1 | 2/2006 | Zeltinger et al. |
| 2006/0076708 A1 | 4/2006 | Huang et al. |
| 2006/0129222 A1 | 6/2006 | Stinson |
| 2006/0134211 A1 | 6/2006 | Lien et al. |
| 2006/0142844 A1 | 6/2006 | Lowe et al. |
| 2006/0149354 A1 | 7/2006 | Shanley et al. |
| 2006/0177480 A1 | 8/2006 | Sung et al. |
| 2006/0229711 A1 | 10/2006 | Yan et al. |
| 2006/0271170 A1 | 11/2006 | Gale et al. |
| 2007/0132155 A1 | 6/2007 | Burgermeister et al. |
| 2007/0132156 A1 | 6/2007 | Burgermeister et al. |
| 2007/0134289 A1 | 6/2007 | Burgermeister et al. |
| 2007/0134296 A1 | 6/2007 | Burgermeister et al. |
| 2007/0135898 A1 | 6/2007 | Burgermeister et al. |
| 2007/0135899 A1 | 6/2007 | Burgermeister et al. |
| 2007/0135900 A1 | 6/2007 | Burgermeister et al. |
| 2007/0135901 A1 | 6/2007 | Burgermeister et al. |
| 2007/0135902 A1 | 6/2007 | Burgermeister et al. |
| 2007/0208411 A1 | 9/2007 | Meyer et al. |
| 2007/0219642 A1 | 9/2007 | Richter |
| 2007/0239258 A1 | 10/2007 | Fischell et al. |
| 2007/0255391 A1 | 11/2007 | Hojeibane et al. |
| 2007/0283552 A1 | 12/2007 | Gale et al. |
| 2007/0290412 A1 | 12/2007 | Capek et al. |
| 2007/0293938 A1 | 12/2007 | Gale et al. |
| 2008/0046068 A1 | 2/2008 | Burgermeister et al. |
| 2009/0096137 A1 | 4/2009 | Williams et al. |

FOREIGN PATENT DOCUMENTS

| | | | |
|---|---|---|---|
| WO | WO 2007/134222 A2 | 11/2007 | |
| WO | WO 2007/134222 A3 | 3/2008 | |

OTHER PUBLICATIONS

Office Action dated Nov. 14, 2008 received in U.S. Appl. No. 11/747,699, filed May 11, 2007.

Amendment and Response to Office Action dated Nov. 14, 2008 received in U.S. Appl. No. 11/747,699, filed May 11, 2007.

Office Action dated Jul. 23, 2009 received in U.S. Appl. No. 11/747,699, filed May 11, 2007.

Office Action dated May 26, 2010 received in U.S. Appl. No. 11/747,699, filed May 11, 2007.

Office Action dated Nov. 19, 2009 received in U.S. Appl. No. 11/747,699, filed May 11, 2007.

* cited by examiner

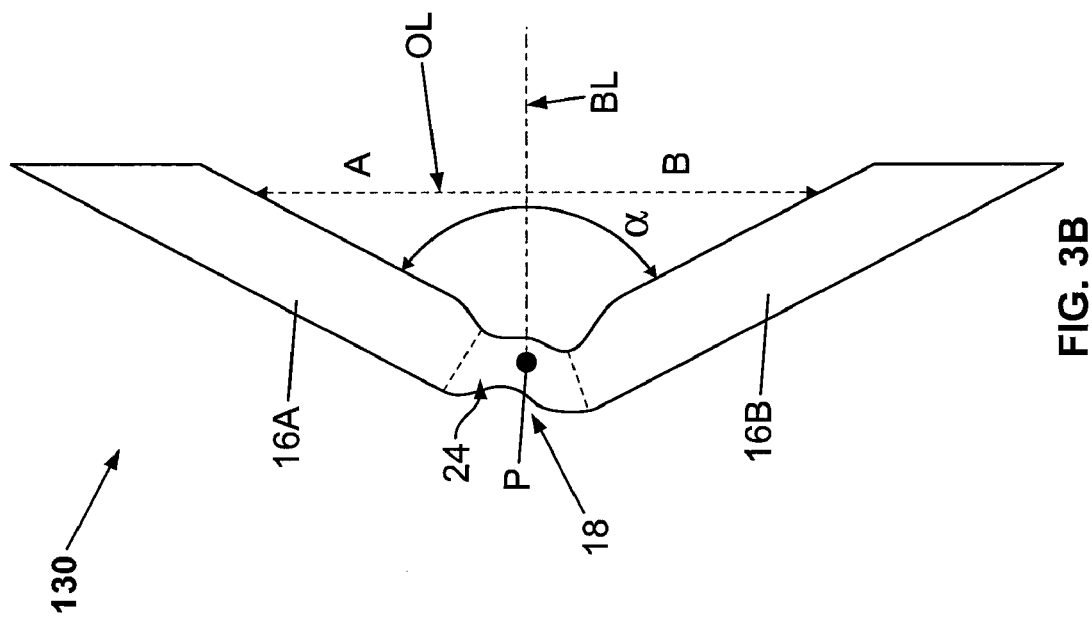
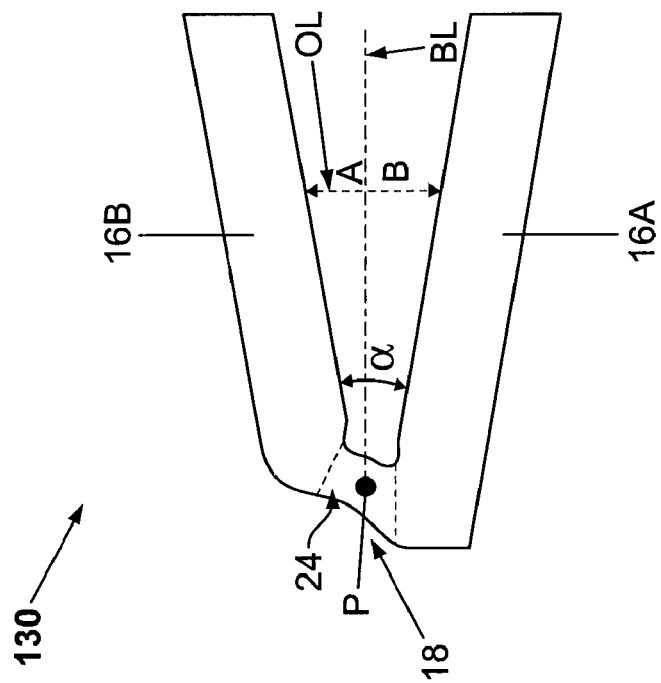
FIG. 3B
FIG. 3A

US 7,972,373 B2

BALLOON EXPANDABLE BIOABSORBABLE STENT WITH A SINGLE STRESS CONCENTRATION REGION INTERCONNECTING ADJACENT STRUTS

FIELD OF THE INVENTION

The present invention relates to expandable, tissue supporting devices implanted within a body lumen of a living animal or human to support the organ or maintain patency and, more particularly, to balloon expandable stents for which deployment is a function of plastic deformation of the stent material.

BACKGROUND OF THE INVENTION

Expandable tissue supporting devices, such as balloon expandable stents, have been developed for implantation within a body passageway. Stents typically include columns of cells of interconnected struts, where each cell constitutes two adjacent struts joined to each other so that the struts rotate away from each other during stent deployment. The struts provide radial strength to a stent upon expansion. The stent struts and interconnections may also serve to contain pharmaceutical agents or bioactives, which are applied through known means, such as in a polymer coating, or housed in reservoirs within the struts or interconnections, to be released into the body following implantation.

As well known in the art, when a stent expands, such as by balloon expansion, the stent is subjected to various stresses and strains (hereinafter collectively "stresses") that lead to plastic deformation of the stent components, such that upon balloon deflation the construct of the stent remains at a desired shape and size.

In addition, the deformation that occurs in certain regions of a stent to effect stent deployment has both an elastic component of strain and a plastic component of strain. Both the volume of stent material stressed, and the ratio of plastic deformation to elastic deformation in this material, largely governs the well-known phenomenon of recoil. It is, therefore, desirable to minimize the volume of material stressed and to maximize the ratio of plastic deformation to elastic deformation within this volume of material. To counter an expected large recoil, the stent often is over-expanded during implantation, which in turn can cause damage to or inflammation of the body passageway.

Stent design efforts have focused, and continue to focus, on addressing the above-mentioned undesirable phenomena associated with stent expansion. For example, stents have been designed to include stress concentration regions, for example, hinges, at selected points, which typically are small and well defined. Hinges are typically areas where the geometry has been reduced to provide that deformation occurs in that region. When a stent having stress concentration regions is expanded, the stresses are localized within these regions, which effectively lowers the volume of material stressed, thereby minimizing stresses in other regions of the stent.

One known stent design includes stress concentration regions, or hinges, at each end of a strut, such that a junction interconnecting adjacent struts includes two stress concentration regions or hinges. See, for example, U.S. Pat. No. 6,241,762 issued Jun. 5, 2001, incorporated by reference herein. Stent designs using known stainless steel or CoCr alloys typically utilize two stress concentration regions per strut, because of limitations in the stress capacity of the material. Both 316L and CoCr alloys typically used for stent manufacture possess an elongation of 40%-50% at break. If stresses during deployment of the stent are so excessive to cause a stent elongation exceeding the stent's elongation at break capacity, the stent is predisposed to cracking and failure. By allowing deformation to occur at either end of the strut, in other words, at the two hinge regions, the level of stress in each hinge region is maintained below the elongation at break capacity of the material. If a similar level of expansion between struts were attempted in only one hinge, the risk exists of exceeding the stress capacity of the material, unless the geometry of the hinge itself is increased sufficiently to reduce the stress levels in the hinge. Conversely, the amount of deformation between struts could be reduced to lower stress levels appropriate for these materials. More struts, however, would be needed to achieve the desired deployment diameter and, thus, more material would be implanted in the body, which is not necessarily desirable.

Hinge regions occupy volume within the stent structure and, consequently, decrease the volume of stent material available for the fabrication of struts, which provide the radial strength and drug delivery functionalities to the stent. Thus, the number of hinges in a column of cells within a stent impacts the geometry of the struts included within the column and, as a result, the strength and drug delivery capacity of the cell column and ultimately the stent itself.

Another stent design that has been developed includes a single stress concentration region, or hinge, within a strut. See, for example, U.S. Pat. No. 6,764,507, issued Jul. 20, 2004 and incorporated by reference herein in its entirety. In such single concentration region within a strut configuration, the material from which the hinge (concentration region) can be fabricated constitutes a limitation upon the amount of stress the hinge can absorb. Based on the materials presently known in the art for fabricating stents, the hinges of a stent having a single concentration region within a strut configuration can only withstand about the same level of stress as the hinges of prior art stents having a two stress concentration region per strut junction configuration. Therefore, to achieve the same expansion angle between struts, the axial length of hinges of prior art stents having a single concentration region within a strut configuration needs to be sufficiently increased, so as to limit higher levels of plastic deformation from the increased concentration of stresses at the single hinges during expansion from causing device failure. This increase in length causes the hinges in the prior art stents with a single concentration region within strut configuration to be longer in length than the hinges of stents having a two concentration region per strut junction configuration. The necessity to increase the axial length of the hinges in a stent, in turn, increases the volume of material used by hinges in a stent, which as discussed above is not desirable.

Accordingly, there exists a need for a balloon expandable tissue supporting device that concentrates stresses on a reduced volume of material in the device and avoids the application of stresses to regions in the device whose desired functionalities can become impaired when subjected to undue stresses.

SUMMARY OF THE INVENTION

In accordance with the present invention, an expandable, implantable medical device, such as a stent, is in the form of a frame structure, such as a polymeric frame structure, having a plurality of hoop components interconnected by a plurality of flexible connectors and joined together to form a substantially cylindrical device. The device is expandable from a cylinder having a first diameter to a cylinder having a second diameter. The hoop components are formed as a continuous series of substantially (axially) longitudinally oriented radial struts and alternating stress concentration junctions. Adjacent struts are substantially parallel when the cylinder is in an unexpanded form at the first diameter. Each of the junctions defines a pivot point for the attached, adjacent struts. When the stent is expanded to a second diameter, stresses are concentrated at the junctions, which act as hinges, and the attached, adjacent struts rotate about the pivot point, substantially symmetrically and uniformly away from each other, to form substantial V-shapes. When the cylinder is at a second diameter, each of the pivot points is located substantially on a line bisecting the V-shapes formed by the struts.

In one embodiment, the junctions have a cross-sectional area smaller than the cross-sectional area of the struts attached to the junctions.

BRIEF DESCRIPTION OF THE DRAWINGS

Other objects and advantages of the present invention will be apparent from the following detailed description of the presently preferred embodiments, which description should be considered in conjunction with the accompanying drawings in which like references indicate similar elements and in which:

FIG. 3A is a planar representation of an exemplary cell of an unexpanded stent according to one embodiment of the present invention.

FIG. 3B is a planar representation of the exemplary cell of the stent shown in FIG. 3A in an expanded configuration.

DETAILED DESCRIPTION OF THE INVENTION

Implantable medical devices may be fabricated from any number of suitable biocompatible materials, including polymeric materials. The internal structure of these polymeric materials may be altered utilizing mechanical and/or chemical manipulation of the polymers. These internal structural modifications may be utilized to create devices having specific gross characteristics, such as crystalline and amorphous morphology and a selected molecular orientation as described in "Balloon Expandable Bioabsorbable Drug Eluting Stent", U.S. Ser. No. 11/747,699 filed May 11, 2007 ("the '699 application"), assigned to the assignee of this application and incorporated by reference herein. Although the present invention of reducing the volume of material in an expandable, implantable device experiencing stress during expansion, by concentrating stresses generated during expansion of the device in a reduced number of small, localized regions, and simultaneously enhancing displacement capabilities of components undergoing displacement during expansion of the device, applies to any number of implantable medical devices, for ease of explanation, the following detailed description will focus on an exemplary stent.

Figure 1:
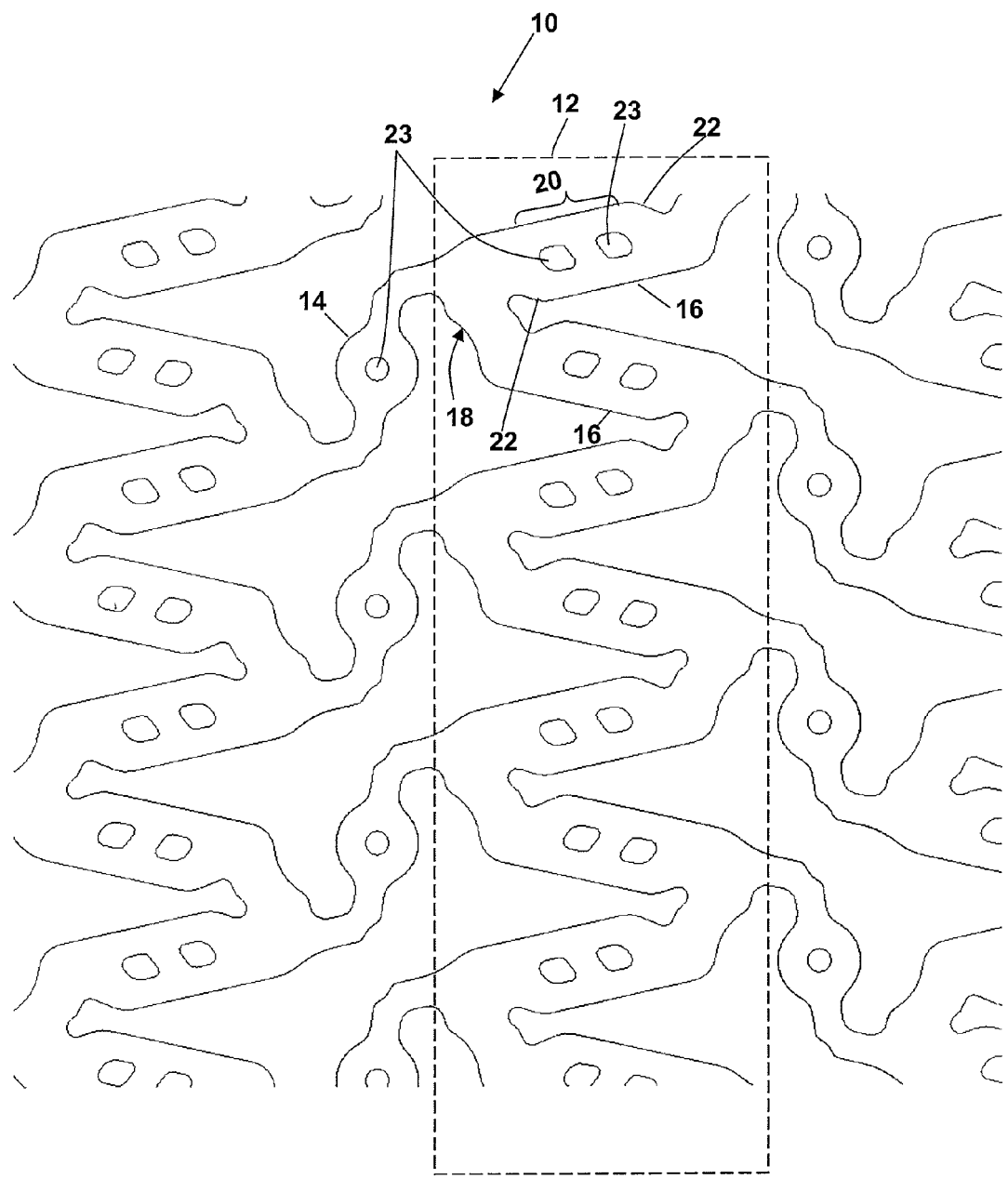
FIG. 1 is a planar representation of a portion of an exemplary, unexpanded stent, in accordance with the present invention.

FIG. 1 illustrates a partial, planar view of an exemplary stent 10, in accordance with the present invention. Referring to FIG. 1, and also to FIG. 2, which is an enlarged view of a portion of the stent 10 shown in FIG. 1, the stent 10 includes a plurality of hoop components 12 interconnected by a plurality of flexible connectors 14. The hoop components 12 are formed as a continuous series of substantially longitudinally (axially) oriented radial struts 16 and alternating stress concentration junctions 18. The combination of the radial struts 16 and the alternating junctions 18 form a substantially sinusoidal pattern. Although shown in planar view, the hoop components 12 are essentially ring members linked together by the flexible connectors 14 to form a substantially tubular or cylindrical stent structure. The resulting cylinder is expandable from a first diameter, where the stent 10 is in an unexpanded configuration with adjacent struts 16 substantially parallel as shown in FIG. 1, to a second diameter, where the stent has been expanded for implantation in a body passageway and the adjacent struts 16 have the general configuration as discussed below in the text accompanying the description of FIG. 3B.

Referring to FIG. 1, the connectors 14 and the struts 16 may include optional openings 23 which are preferably loaded with an agent, such as a drug, for delivery to the body passageway in which the stent 10 is implanted. For a listing of potential agents, see, for example, the '699 application.

Although the hoop components 12 may be designed with any number of design features and assume any number of configurations, in the exemplary embodiment of the stent 10, the radial struts 16 are wider in their central regions 20 than at ends 22. This design feature may be utilized for a number of purposes, including improving radial strength or stiffness of the device or increasing the area that may contain openings to house an agent.

In accordance with the present invention, the geometry and material characteristics of, and the interconnections between, the struts 16 and the junctions 18 in the stent 10 provide that cells in a column of struts 16 include a single stress concentration region 24 within the junction 18 interconnecting two adjacent struts 16, and that the adjacent struts 16 of a cell rotate uniformly and symmetrically away from each other, about a pivot point P in the stress concentration region 24, to form a substantial V-shape during stent expansion. The concentration of stresses at the relatively small, predetermined regions 24 of the stent 10 located within the junctions 18, during stent expansion, results in what is often referred to as "hinging", where the hinge is the small, concentration region 24 within which the stresses are very high during stent expansion. The junction 18, for example, can constitute a ductile hinge, as conventionally known in the art.

Figure 2:
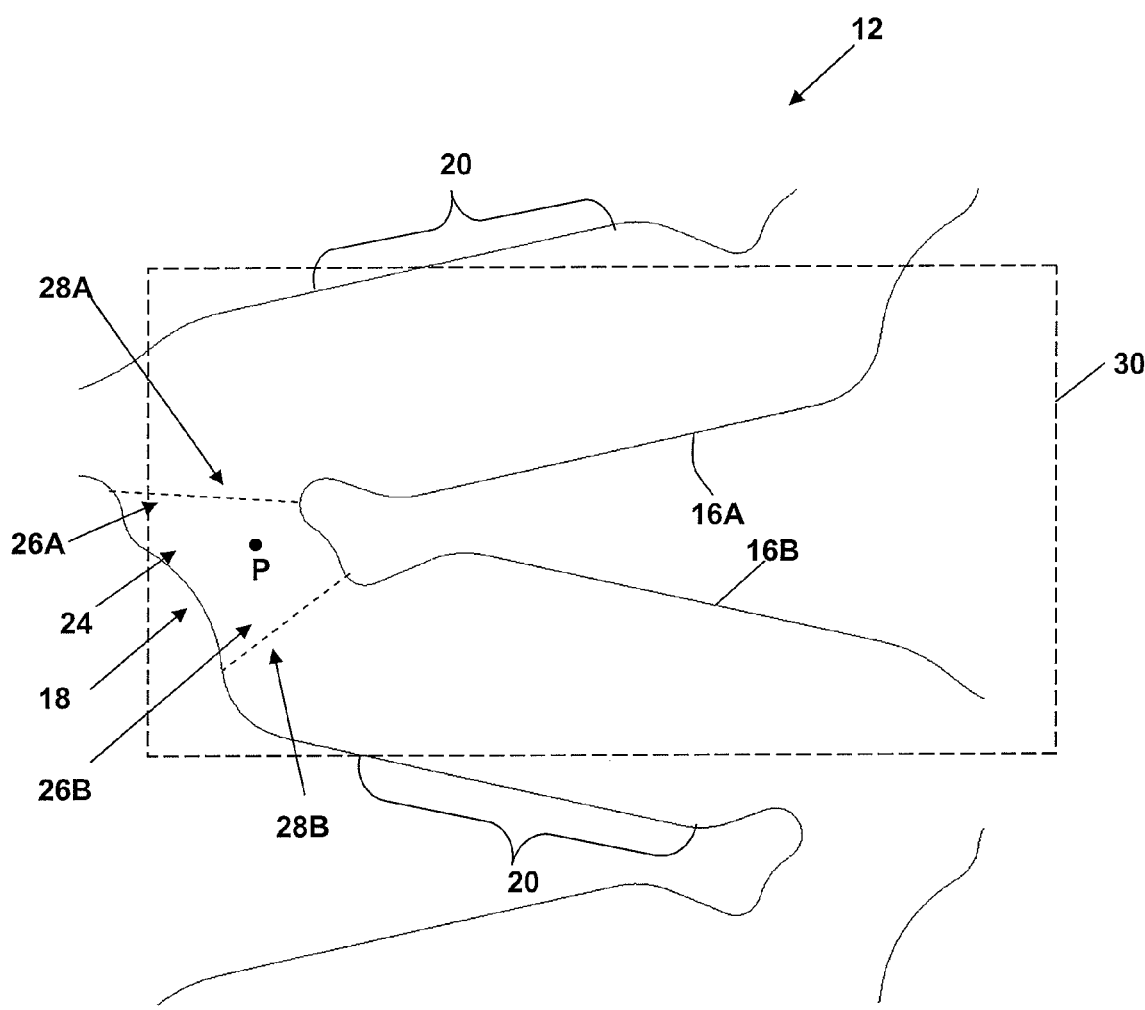
FIG. 2 is an enlarged view of a portion of the planar representation of the stent of FIG. 1.

Referring to FIG. 2, which illustrates an exemplary cell 30 of the stent 10 including adjacent struts 16 interconnected at a junction 18, and where the openings in the struts 16 for containing agents are omitted, the stress concentration or hinge region 24 within the junction 18 includes ends 26A and 26B interconnected to end portions 28A and 28B, respectively, of the adjacent struts 16A and 16B. The hinge region 24 preferably has a small cross-sectional area relative to the adjacent geometry of the struts 16. In addition, the cross-sectional area of the central region 20 of the struts 16A and 16B is substantially larger than the cross-sectional area of the hinge region 24. Based on these geometrical differences, when the stent 10 is expanded, stresses are localized and concentrated in the hinge region 24, and the struts 16A and 16B rotate substantially symmetrically and uniformly away from each other, centered about the pivot point P in the region 24. When the stent 10 is expanded, the struts 16A and 16B of the cell 30 define a substantial V-shape, where the vertex of the V-shape is at the point P and a line bisecting the V-shape extends generally through the point P.

FIG. 3A is a planar representation of a cell 130 of a stent in the unexpanded (undeformed) configuration, according to one embodiment of the present invention. FIG. 3B is a planar representation of the cell 130 of FIG. 3A in the expanded (deformed) configuration. Referring to FIG. 3A, the cell 130 includes substantially parallel adjacent struts 16A and 16B interconnected to each other at the junction 18. Referring to FIG. 3B, as discussed above, in the expanded cell 130, the struts 16A and 16B form a substantial V-shape and a line BL bisecting the V-shape formed by the struts 16A, 16B extends through the pivot point P in the region 24. During stent expansion, the struts 16A and 16B of the cell 130 rotate symmetrically and uniformly away from each other, about the pivot point P within the hinge region 24 located in the junction 18, to form the V-shape. Therefore, in the expanded cell 130, a distance A from the line BL to the strut 16A is equal or substantially equal to a distance B from the line BL to the strut 16B, where the distances A and B are measured along a line OL orthogonal to the line BL and extending between the struts 16A and 16B.

In one embodiment of the inventive stent, the junction 18 is of a reduced cross-sectional area compared to adjacent struts. Thus, when the stent is expanded, stresses concentrate and are localized substantially in the hinge region 24.

In another embodiment of the inventive stent, referring to FIG. 3B, the junction 18 is constructed to have a geometry and from predetermined materials so that the adjacent struts 16 forming the V-shape of the cell 130 when the stent is expanded are rotatable about the point P, and symmetrically and uniformly rotate away from the line BL to define an angle α between the adjacent struts 16 of up to about 180°.

In alternative embodiments, the ends of the flexible connectors 14 may be connected at different locations to the hoop elements 12 than as shown in FIG. 1. For example, the connectors 14 may conceivably be connected at any point along the struts 16 or outside of the junctions 18. The number of flexible connectors 14 connecting adjacent strut columns can vary from one flexible connector to as many flexible connectors as there are cells. Further, it is to be understood that the flexible connectors 14 may have any desired shape, any number of design features and any number of configurations, as described, for example, in the '699 application. The only limitation on the construction of the connectors 14, and the location of the connections of the flex connector 14 to the hoop elements 12, in a stent or like implantable device, is that the combination of the construction and the connection of the connector 14 does not interfere with the hinge region 24 acting as a stress concentrator and providing for symmetrical rotation of the adjacent struts 16 of a cell away from each other, about the pivot point P in the junction 18, to form a V-shape when the stent is expanded.

In one embodiment of the inventive stent, the struts 16 are preferably fabricated from a material that makes the struts 16 stiffer in bending than the junctions 18. Therefore, during expansion of the stent, the struts 16 resist deformation more than the junction 18. Consequently, the hinge regions 24 at the ends of adjacent struts 16, which are not as stiff as the struts 16, become stress concentrators and carry all or the majority of the deformation during expansion. As all or the majority of the deformation is localized in the hinge regions 24, the hinge regions 24 accommodate substantially all of the expansion of the stent, and other regions of the stent, such as the struts 16, advantageously do not experience any significant stress during expansion. The struts, which generally are low stress regions, can therefore optionally include strategically placed openings to house an agent, such as a radiopaque agent.

The materials from which the junction 18 of the inventive stent is fabricated preferably have the characteristic of elongation at break occurring well into the plastic region of deformation. The materials of the junction 18, for example, include the polymeric materials described in the '699 application. Materials having elongation at break occurring well into the plastic region of deformation, for example, materials having greater than the 40-50% elongation at break capacity of current metals used in stents, are preferred, such that stresses can be localized at the junctions 18 and, therefore, away from all or substantially all other regions of the stent.

In another embodiment of the inventive stent, the components of the stent are formed with any polymeric material, such as described in the '699 application, so long as when the stent is expanded the stresses are concentrated and localized in the junctions 18.

The inventive stent having a single hinge region per strut junction configuration, hence, provides the following advantages over prior art stent designs. The use of a single hinge region per strut junction configuration, for example, in a polymeric stent system, reduces the number of hinge regions in a column of cells and, thus, the volume of material that undergoes deformation during stent expansion. The reduction of the number of hinge regions, and also the reduction of the overall volume of material functioning as a stress concentration region, in a stent, in turn, enhances the level of stresses in the deformed regions, creating a high ratio of plastic strain to elastic strain to reduce stent recoil.

The capability of constructing a stent of given dimensions with a decreased number of smaller, predefined hinge regions, based on the single hinge region per strut junction configuration of the invention, provides for several beneficial implementations in an existing stent design, without changing the overall dimensions of the stent. First, the cell column of a stent can have an axial length less than the axial length of a cell column in a prior art stent, and yet still have a radial strength and stiffness comparable to the cell column in the prior art stent. In addition, the axial length of individual cell columns in a stent can be decreased, such that an increased number of cell columns can be included within a stent of the same overall axial length, which is beneficial for overall stent radial strength and stiffness. Further, the axial length of the struts of the cells in a column of a stent can be increased, without increasing the overall axial length of the column, thereby providing for increased strength and stiffness for an existing stent design and more space to house an agent if desired.

Further, the use of a single hinge region for interconnecting the ends of adjacent struts to each other in a cell, in accordance with the present invention, concentrates all or substantially all of the stresses at the single hinge region, such that all or substantially all such stresses are removed from all or substantially all of the struts when the stent is expanded. Therefore, all or substantially all of the struts can be used for drug reservoirs.

In addition, the reduction of stress on struts, and also on material in a stent other than the material of the stress concentration junctions, during stent expansion reduces recoil of struts and such other stent material, following expansion of the stent, for example, within a lumen. For example, in a polymeric stent system having a single hinge region per strut junction configuration, where the polymer material components in the hinge region have significant elongation at break and locally become of reduced cross-section as they deform, the volume of material in a stent stressed during expansion is reduced, thereby reducing recoil.

Further, selected polymeric materials having an increased capacity to absorb stress, such as polymers having molecular orientation, polymers having plasticizers and polymer blends as described in the '699 application, can be utilized to fabricate the stress concentration junctions in the inventive stent. By use of such materials, the inventive stent can include smaller, localized regions that can absorb more stress than comparable stress concentration regions in prior art stents, thereby further reducing the total volume of material in a stent absorbing stress.

The following examples are illustrative of the principles and practice of this invention, although not limited thereto. Numerous additional embodiments within the scope and spirit of the invention will become apparent to those skilled in the art once having the benefit of this disclosure.

Example 1

The performance of a stent having the inventive single hinge region per strut junction configuration was empirically compared with a stent having cells with a two hinge regions per strut junction configuration. In the experimentation, two stents were each laser cut from extruded tubing (Dunn Industries, Inc.) using a low energy excimer laser. The tubes were composed of a 20/80 (w/w) blend of 10/90 (mol/mol) poly (lactide-co-glycolide) (PLGA, IV=1.53, HFIP)/85/15 (mol/mol) PLGA (IV=3.2, $CHCl_3$) with an outside diameter (OD) of 1.45 mm and an inside diameter (ID) of 1.04 mm. The stents were mounted on a 3.0 mm balloon dilatation catheter, heated for 1 minute in a 37° C. water bath, and then expanded using pressurized saline (10 atm) to a final size of 3.0 mm OD×18 mm in length with a wall thickness of 200 microns. The first stent had a two hinge region per strut junction configuration, such as described in U.S. Pat. No. 6,241,762 issued Jun. 5, 2001, incorporated by reference herein, including 12 columns of struts, with each column including six cells, and the second of the stents had a single hinge region per strut junction configuration, in accordance with the present invention, including 13 columns of struts, with each column including six cells. The second stent had the single hinge region per strut junction configuration as described herein. The single hinge region per strut junction configuration was found to have a radial strength of 13.9 psi, and the stent with the conventional two hinge region per strut junction configuration was found to have a radial strength of 10.6 psi. In other words, the inventive stent had a 31% greater radial strength than the prior art stent with the two hinge region per strut junction configuration. In addition, after the two stents had been immersed in a 38° C. water bath for 21 days, the stent having the two hinge region per strut junction configuration was found to have a recoil of 11.8% from maximum expansion, whereas the inventive stent with the single hinge region per strut junction configuration was found to have an 11.6% recoil from maximum expansion.

Example 2

Endovascular stent surgery is performed in a cardiac catheterization laboratory equipped with a fluoroscope, a special x-ray machine and an x-ray monitor that looks like a regular television screen. The patient is prepared in a conventional manner for surgery. For example, the patient is placed on an x-ray table and covered with a sterile sheet. An area on the inside of the upper leg is washed and treated with an antibacterial solution to prepare for the insertion of a catheter. The patient is given local anesthesia to numb the insertion site and usually remains awake during the procedure. A polymer stent having a single hinge region per strut junction configuration, such as described in Example 1, having an outside diameter of 1.45 mm and a wall thickness of 200 microns is mounted onto a traditional 3.0 mm balloon dilatation catheter. To implant a stent in the artery, the catheter is threaded through an incision in the groin up into the affected blood vessel on a catheter with a deflated balloon at its tip and inside the stent. The surgeon views the entire procedure with a fluoroscope. The surgeon guides the balloon catheter to the blocked area and inflates the balloon, usually with saline to about 10 atm or according to instructions for use of the catheter, causing the stent to expand and press against the vessel walls. The balloon is then deflated and taken out of the vessel. The entire procedure takes from an hour to 90 minutes to complete. The stent remains in the vessel to hold the vessel wall open and allow blood to pass freely as in a normally functioning healthy artery. Cells and tissue will begin to grow over the stent until its inner surface is covered.

Although preferred embodiments of the present invention have been described and illustrated, it will be apparent to those skilled in the art that various modifications may be made without departing from the principles of the invention.

What is claimed is:

1. A method of using an implantable medical device in a surgical procedure, said medical device comprising first and second cylindrical hoops arranged to define a single longitudinal axis and radially expandable about said axis from an unexpanded state to an expanded state, said first and second hoops joined one to the other by a plurality of flexible connectors, at least one of said hoops including a plurality of pairs of elongated struts that are substantially longitudinally oriented relative to said axis in said unexpanded state, each of said pairs of struts comprising adjacent first and second struts arranged substantially alongside each other, so as to define an acute angle between said first and second struts in their unexpanded state, said first and second struts having respective end portions adjacent each other and joined to each other by a junction, said first strut having an inner edge and an outer edge opposite said inner edge of said first strut, said second strut having an inner edge and an outer edge opposite said inner edge of said second strut, said inner edge of said first strut being opposed to said inner edge of said second strut, said junction having an inner edge and an outer edge opposite said inner edge of said junction, said inner edge of said junction being continuous with said inner edge of said first strut and said inner edge of said second strut, at least a portion of said inner edge of said junction being convex relative to an imaginary point located between said inner edge of said first strut and said inner edge of said second strut, said at least a portion of said inner edge of said junction intersecting an imaginary line bisecting the acute angle, said junction including a hinge region, and said hinge region being less rigid than said first and second struts, wherein at least one of said flexible connectors is joined directly to one of said first struts, said method comprising the steps of:

implanting said medical device into a body passageway with said first and second hoops in said unexpanded state; and expanding said at least one of said hoops to said expanded state, such that said first and second struts move uniformly and symmetrically away from the imaginary line bisecting the acute angle in response to the radial expansion of said at least one of said hoops and flex said junction such that stresses generated in said junction during said expanding step are concentrated at said hinge region.

2. The method of claim 1, wherein said hinge region is more ductile than said first and second struts.

3. The method of claim 1, wherein, when said at least one of said hoops is in said expanded state, said stresses are concentrated within said hinge region.

4. The method of claim 3, wherein said concentrated stresses in said hinge region exceed the yield point of said hinge region.

5. The method of claim 4, wherein said concentrated stresses in said hinge region are below the ultimate stress levels of said hinge region.

6. The method of claim 1, wherein said hinge region comprises a polymer having a predetermined molecular orientation.

7. The method of claim 1, wherein said at least one of said hoops is formed from polymeric materials.

8. The method of claim 1, wherein said junction has cross-sections outside of said hinge region and said hinge region has cross-sections that are smaller than said cross-sections of said junction.

9. The method of claim 1, wherein said at least one of said flexible connectors is joined to said one of said first struts such that said hinge region is entirely offset to one side of said at least one flexible connector.

10. The device of claim 1, wherein at least a portion of said outer edge of said junction is convex toward the imaginary point.

11. The device of claim 1, wherein said outer edge of said first strut is continuous with said flexible connector.

12. The device of claim 1, wherein said outer edge of said second strut is continuous with said outer edge of said junction.

* * * * *